US007513251B2

(12) United States Patent
Blum

(10) Patent No.: US 7,513,251 B2
(45) Date of Patent: Apr. 7, 2009

(54) HAND-HELD POTASSIUM SUPER OXIDE OXYGEN GENERATING APPARATUS

(76) Inventor: Mel Blum, 1385 Lyon Pl., Wantagh, NY (US) 11793

( * ) Notice: Subject to any disclaimer, the term of this patent is extended or adjusted under 35 U.S.C. 154(b) by 489 days.

(21) Appl. No.: 11/150,122

(22) Filed: Jun. 13, 2005

(65) Prior Publication Data

US 2006/0280658 A1 Dec. 14, 2006

(51) Int. Cl.
*A61M 15/00* (2006.01)

(52) U.S. Cl. ............................ 128/202.26; 128/200.24; 128/204.22

(58) Field of Classification Search ............ 128/200.24, 128/202.12, 202.21, 202.26, 204.22, 205.26
See application file for complete search history.

(56) References Cited

U.S. PATENT DOCUMENTS 3,202,150 A * 8/1965 Miller .................. 128/205.12
3,702,110 A * 11/1972 Hoffman et al. .............. 60/279
3,860,396 A 1/1975 Finley
3,938,512 A 2/1976 Mausteller et al.
3,942,524 A 3/1976 Li et al.
4,265,238 A * 5/1981 Swiatosz et al. ....... 128/205.12
4,325,364 A 4/1982 Evans
5,267,558 A 12/1993 Haertle et al.
5,620,664 A 4/1997 Palmer
5,690,099 A 11/1997 Abramov et al.
6,957,651 B2 * 10/2005 Nuckols et al. ........ 128/200.24

* cited by examiner

*Primary Examiner*—Steven O Douglas
(74) *Attorney, Agent, or Firm*—Oliff & Berridge, PLC

(57) ABSTRACT

A hand-held oxygen generating apparatus that includes a container containing potassium super oxide and valves that regulates oxygen and air flow.

23 Claims, 2 Drawing Sheets

HAND-HELD POTASSIUM SUPER OXIDE OXYGEN GENERATING APPARATUS

BACKGROUND

Emergency breathing apparatuses that provide oxygen to the user are known. Some provide oxygen directly, such as those that employ compressed or liquid oxygen. Others provide oxygen through a chemical reaction.

Conventional chemical oxygen generators may contain alkali metal chlorate candles, which are burned to produce oxygen. Other conventional chemical oxygen generators may contain potassium super oxide, which reacts with carbon dioxide to produce oxygen. Conventional chemical oxygen generators are generally used by miners, firefighters, military personal and the like to provide emergency oxygen when needed.

For example, U.S. Pat. No. 5,690,099 to Abramov et al. discloses a closed-circuit breathing system that includes a mask and a canister containing, for example, $KO_2$. The canister contains one or more working compounds formed of a peroxide and/or superoxide of one or more metals of the alkali and alkaline-earth metal groups such as $KO_2$ and $CaO_2$ and a moisture releasing material such as wetted activated charcoal is utilized to replenish the oxygen and absorb the carbon dioxide in exhaled air. The canister includes an inlet port for receiving exhaled air, and an outlet port for providing breathable air for inhalation. The patent describes that the canister can be used in a closed or semi-closed circuit breathing system worn by a user such as a fireman, miner etc.

U.S. Pat. No. 3,938,512 to Mausteller et al. discloses an emergency breathing apparatus that includes a mask having breathing opening, directly in front of the outer end of which there is a chemical cartridge that is secured to the mask. The cartridge has an exhalation passage extending through it from front to back, with its rear end registering with the breathing opening. A check valve in the inhalation passage allows air flow only into the mask. In the exhalation passage there is a carbon dioxide removing and oxygen generating chemical. A breathing bag is supported by the cartridge and communicates with the front end of the exhalation passage. The mask is provided with an inhalation check valve allowing air being inhaled from the bag to bypass the chemical.

U.S. Pat. No. 5,267,558 to Haertle et al. discloses a chemical cartridge for respirators, the cartridge containing a chemical, e.g., potassium hyperoxide, which when acted upon by carbon dioxide and moisture, produces oxygen from a stream of inhaled air. Two discharge nozzles are provided, which project into the chemical and out of which the regenerated exhaled air flows. The incoming flow occurs over a large area and the outflow occurs over a small area with the peripheral surfaces of the discharge nozzles being spaced substantially equidistant from an inlet surface of the chemical, thereby ensuring optimum use of the chemical for oxygen production purposes because a user's exhaled air is caused to flow completely through the entire space occupied by the chemical.

U.S. Pat. No. 3,942,524 to Li et al. discloses an emergency breathing apparatus that includes a canister containing layers of $KO_2$ particles separated by parallel screen assemblies, the upper two screen assemblies being connected by a vertical bypass screen near the canister inlet. The layered $KO_2$ bed is effective to remove $CO_2$ from exhaled breath, and generate oxygen for recharging the air prior to inhalation. The canister inlet is connected by a flexible hose to the exhalation side of a breather mouthpiece, the inhalation side of the mouthpiece being connected to the upper end of the inhalation chimney. Communication between the canister outlet and the lower end of the inhalation chimney is provided by a breather bag, fitted with a set of baffles to define a tortuous flow path for cooling the processed air. A collector mounted at the canister outlet prevents liquid $KO_2$ (which forms KOH) from entering the breather bag. To protect the user and confine the heat within the canister, the canister is insulated.

U.S. Pat. No. 3,860,396 to Finley discloses a light-weight, portable oxygen generator containing an alkali metal chlorate candle. The generator includes a generally tubular housing, preferably formed of extruded aluminum or other heat-conducting metal, and preferably includes longitudinally-extending ribs which serve to dissipate heat generated inside of the housing. The generator also includes a dispensing valve through which oxygen passes.

U.S. Pat. No. 5,620,664 to Palmer discloses a light-weight, personal, portable oxygen dispenser that includes a cylindrical body. The cylindrical body is a light-weight material, such as extrudable aluminum, with a fluted or ridged exterior configuration to minimize heat conductivity to the fingers of someone holding the dispenser while it is operating.

U.S. Pat. No. 4,325,364 to Evans discloses a training breathing apparatus that includes a disposable canister filled with a reagent that creates heat by reacting with the moisture in exhaled breath.

SUMMARY

Despite these various designs, conventional portable oxygen generators pose substantial drawbacks that either limit their use, or limit their use by a wide range of individuals that otherwise could benefit from their use. For example, professionals that are used to using such portable oxygen generators are constrained by the weight, material quality, construction, or heat generation of such devices. Likewise, these issues of weight, quality, construction, and heat generation also tend to prohibit such oxygen generators from being used by non-professionals, such as athletes or the like. Moreover, many of the conventional oxygen generators cannot be transported on commercial aircraft due to potential safety problems and leakage from cabin air pressure. The present disclosure thus seeks to overcome these disadvantages of the prior art, and provide improved portable oxygen generators.

For example, conventional potassium super oxide oxygen generators are generally bulky and must be worn in a harness. Furthermore, the chamber in which the active ingredient is held is usually made from heavy, high grade stainless steel. For example, conventional potassium super oxide oxygen generators can weigh between 4.5-7.5 kg.

Applicant has identified a need for potassium super oxide oxygen apparatuses in which the oxygen reaction is slowed down to decrease heat generation, thereby allowing the apparatus to be hand-held. Such hand-held generators may be used, for example, by people escaping fires, by skiers, by mountain climbers, by asthmatics, by people with emphysema, by people suffering from altitude sickness, and by athletes. Such hand-held generators may be also used as backup oxygen generators for Emergency Medical Service (EMS) squads, fire departments, miners, and the like, should their regular emergency oxygen become depleted.

BRIEF DESCRIPTION OF THE DRAWINGS

Various embodiments will be described in detail, with reference to the following figures, wherein.

DETAILED DESCRIPTION OF EMBODIMENTS

Figure 1A:
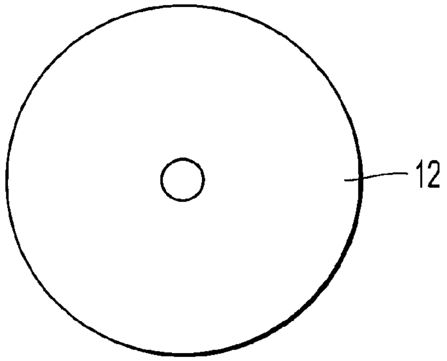
FIG. 1A illustrates a graphite or carbon fiber fabric.

The disclosure is directed to a portable, light-weight, hand-held oxygen generating and breathing apparatus. As one breathes into the apparatus, the carbon dioxide and moisture from the breath react with the potassium super oxide, thus liberating heat and warm dry oxygen. As illustrated in FIGS. 1B, 2A, 2B, and 2C, embodiments of the apparatus (1) may include a mask (6) or (11) or a mouth piece (7), a container (2) containing potassium super oxide (3), and a valve (12) that regulates oxygen flow.

In embodiments, the container may be made of aluminum or other light-weight metal. For example, other suitable metals that may be used to form the container include aluminum alloys, tin, steel (such as stainless steel and carbon steel), and the like. While aluminum is preferred in terms of its light weight, such other metals may be used depending upon the size of the container and its intended use. For example, where the container is expected to be relatively small, the selection of a specific metal may be less important because the weight of the metal becomes less of a concern. In various other embodiments, the container may be made of ceramics, fiber glass, tempered (shatter-proof) glass, and TEFLON®.

In embodiments, the interior of the container is preferably coated so that the active ingredients inside of the container do not react with the container. For example, various chemical-resistant coatings are known in the art, and can readily be incorporated into a protective coating layer primarily for the inside of the container. Such suitable chemical-resistant coatings include, but are not limited to, halogenated materials such as HALAR® ethylene-chlorotrifluoroethylene copolymer (ECTFE) (Allied Chemical Corporation, Morristown, N.J.), TEFZEL® ethylene-tetrafluoroethylene (ETFE) (E.I. duPont de Nemours and Co. Wilmington, Del.), tetrafluoroethylene (TFE), TEFLON® polytetrafluoroethylene (PTFE), polytetrafluoroethylene fluorinated ethylene propylene (PTFE-FEP), polytetrafluoroethylene perfluoroalkoxy (PTFE-PFA), polyvinylidene fluoride (PVDF), polyethylene, polypropylene, and the like. In embodiments, TEFLON® (polytetrafluoroethylene or PTFE) is particularly preferred, in terms of its chemical properties and ready commercial availability.

In embodiments, the container may be jacketed with an insulating and/or heat-dissipating jacket. The insulating jacket may be made of, for example, silicone rubber or other insulating material. The insulating jacket may be ribbed on the inside surface, on the outside surface, or on both of the inside and the outside surfaces. Such ribs may be helpful, for example, in further insulating the user from heat generated inside the container, by providing a decreased surface area for heat to transfer from the container wall, to the insulating jacket, and thereafter to the user. Alternatively, or in addition, the container can include a heat-dissipating jacket to remove some of the heat generated within the container but while not transferring that heat to the user. The container may optionally include a connector for more convenient use. For example, the container can include a lanyard or strap to enable the apparatus to be worn around the neck of a user; a clip to enable the apparatus to be clipped to a belt, utility strap, or the like; a hook-and-loop connector to enable the apparatus to be attached to a mating hook-and-loop connector; or the like. Two or more connectors can be included, for example to provide alternative connection options. In embodiments, the container is preferably disposable and replaceable. However, in embodiments, the apparatus can be re-usable to minimize waste.

The term "potassium super oxide" encompasses a mixture of potassium monoxide ($K_2O$), potassium peroxide ($K_2O_2$), and superoxide ($KO_2$), where superoxide represents about 90% to about 95% of the potassium super oxide. In embodiments, the container contains the potassium super oxide in the form of, for example, a pellet(s), a granule(s) or a laminated sheet(s). In embodiments, the amount of potassium super oxide may range from about 100 g to about 200 g. In order to accommodate the potassium super oxide, the container may be of sufficient size to contain 6-10 ounces. Of course, it will be understood that lesser amounts of potassium super oxide can be used for smaller or shorter-use containers, such as amounts ranging from about 50 g to about 100 g, and that greater amounts of potassium super oxide can be used for larger or longer-use containers, such as amounts ranging from about 200 g to about 500 g or more. However, the container should be of a size limited to containing 16 ounces or less. Containers of a size to contain more than 16 ounces are no longer hand-held units, and would require that the user clip the apparatus to a belt or hang the apparatus around the neck using a neck strap.

Figure 1B:
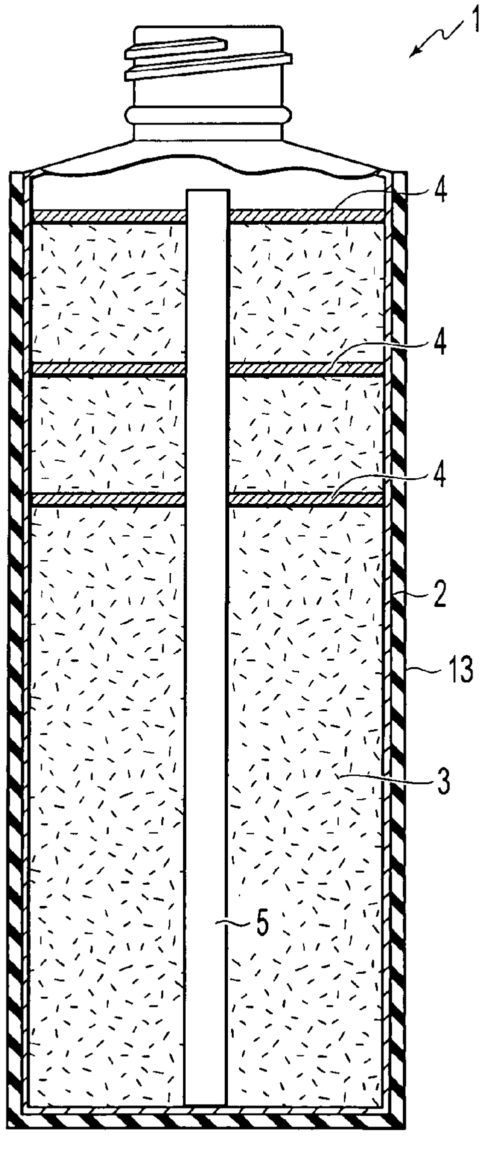
FIG. 1B illustrates one embodiment of the container of an oxygen generating and breathing apparatus.
Figure 2A:
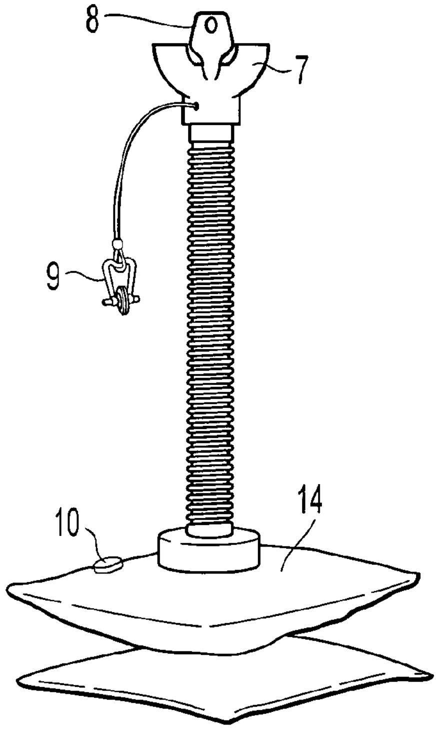
FIG. 2A illustrates one embodiment of a mask and a mouth piece.
Figure 2B:
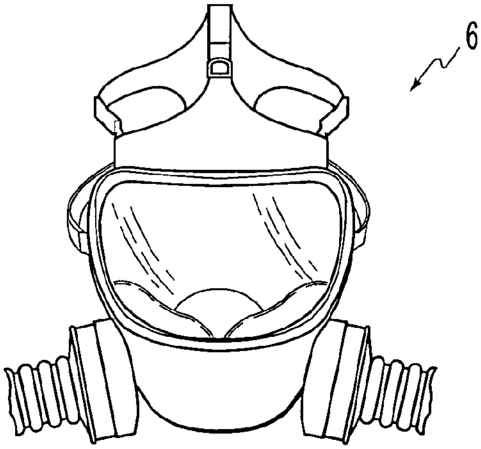
FIG. 2B illustrates a second embodiment of a mask and a mouth piece.
Figure 2C:
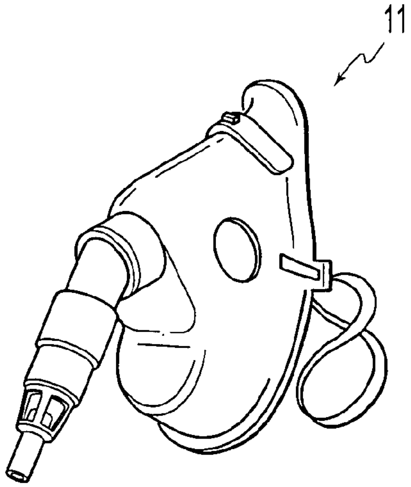
FIG. 2C illustrates a third embodiment of a mask and a mouth piece.

In various embodiments, the container may contain graphite or carbon to help regulate moisture absorption and reduce the exotherm. The graphite or carbon may be in the form of, for example, graphite or carbon fiber fabric(s). For example, FIG. 1B illustrates one embodiment in which a container (2) containing graphite fiber fabrics (4). In embodiments, the thickness of the graphite or carbon fiber fabric(s) may range from about 1 mm to about 6mm. The graphite and carbon fiber fabric(s) eliminate the need for a screen by acting as a filter to prevent the passage of any $KO_2$ dust particles. In various other embodiments, the container may contain anhydrous LiOH to help regulate moisture absorption and reduce the exotherm.

In various embodiments, graphite or carbon fiber fabric(s) may be layered between every 25 mm to 75 mm of potassium super oxide, present as a pellet(s), a granule(s) or a laminated sheet(s). In various other embodiments, the potassium super oxide may be present in the form of sheets, and the graphite or carbon fiber fabric(s) may be placed on the bottom and around the inside of the cylinder.

In embodiments, the container may contain one or more catalysts, adjuvants, and/or initiators. The catalysts may be, for example, one or more of $NaO_2$, $Na_2O$, $Na_2O_2$, $Ca_2O_2$, $Ba_2O_2$, $Li_2O_2$, oxides of rubidium, and oxides of cesium. In embodiments, the catalyst is preferably selected from $NaO_2$ and $Na_2O_2$. The catalyst may serve to reduce the amount of heat produced by the oxygen-generating reaction, and further may slow down the reaction time. The initiator may be, for example, one or more of copper oxychloride, $CuCl_2$, and CuCl. In various embodiments, the amount of initiator present in the container is about 0.5% to 1.0% of the total weight of chemical compounds in the container. In various embodiments, the amount of the one or more catalysts, adjuvants, and/or initiators present in the container is about 5% to 10% of the total weight of chemical compounds in the container. In various embodiments, the ratio of the amount of the one or more catalysts, adjuvants, and/or initiators to the amount of potassium super oxide is about 10:90.

In embodiments, the container may contain a stainless steel tube containing sodium- potassium eutectic alloy in liquid form (NaK), which absorbs heat generated during the reaction. The stainless steel tube may be present as a straight tube, such as the stainless steel tube (5) in FIG. 1B or may be present as a coil, which is capable of absorbing more heat than the straight tube. In embodiments, the stainless steel tube may have a small diameter. For example, the stainless steel tube may have a diameter of about 6 mm to about 8 mm. Furthermore, the stainless steel tube may have thin walls having a thickness of about 1 mm. The length of the stainless steel tube may vary depending on the size of the container. For example, in embodiments, the stainless steel tube may have a length of about 100 mm to about 150 mm. In various embodiments, the stainless steel tube extends from about the top to about the bottom of the container.

In embodiments, the apparatus includes one or more valves, which generally help to regulate air and/or oxygen flow. For example, the apparatus may include at least one valve, located in the flow path between the mask and the container, to regulate air and/or oxygen flow. Although not limited to any particular valve design, a master turn-type valve (such as a knob) is preferred in embodiments, in view of its ease of use. Other valve designs can also be used, such as sliding valves, pressure valves, lever valves, combinations of intake, output, and check valves, and the like. In one particular embodiment, the valve includes a polymeric knob that can be easily turned on and off as needed to regulate the flow of air and/or oxygen. In embodiments, such a valve type is preferred because this valve type is easy for a user to operate, and the polymeric construction of the knob helps to reduce heat transfer from the container to the knob.

In embodiments, the apparatus may include a mask or mouth piece. In embodiments, the mask may be designed to fit snugly over the nose and the mouth of the person wearing the mask, such as the mask (11) illustrated in FIG. 2C. In various other embodiments, the mask may be a full mask that covers the eyes, such as the mask (6) illustrated in FIG. 2B. Masks for such uses are well known in the art, and can be readily adapted for use with the disclosed apparatus. In various other embodiments, a mouth piece may be used in combination with a nose clip, such as the mouth piece (8) and nose clip (9) illustrated in FIG. 2A. In various embodiments, a mouth piece may be used in combination with a bellows or a bag having a relief valve, such as the mouth piece (8) and the bag (14) and relief valve (10) illustrated in FIG. 2A.

In embodiments, the potassium super oxide oxygen generating apparatus weighs between about 250 g and 750 g, and may generate about 10-20 minutes of emergency oxygen, depending on the amount of super oxide present in the container and the amount of exertion by the user. In various embodiments, an oxygen-generating reaction can generate up to 100-120 degrees. In various embodiments, the apparatus may include an NaK alloy tube and a bellows or bag with a relief valve, which in combination can cool breathable air to about 30° C. to about 30° C., or to less than 30° C.

The above-described oxygen generating apparatus offers many benefits over conventional pressurized oxygen generators. For example, the components used in the above-described oxygen generating apparatus are non-hazardous and leak-proof, containing no compressed gas, opening the possibility for use as an emergency breathing apparatus on commercial airplanes. Furthermore, for example, the light-weight components and the slowed heat generation of the above-described oxygen generating apparatus allows it to be used for various hand-held uses. In particular, the above-described oxygen generating apparatus may be useful as an emergency breathing apparatus for escaping fires, as an oxygen supplement for athletes (including skiers and mountain climbers), and as a treatment for various health conditions (including asthma, emphysema, and altitude sickness). Still further, for example, the above-described oxygen generating apparatus offers the advantage of being light-weight, disposable, and replaceable.

While this invention has been described in conjunction with the embodiments set forth above, it is evident that many alternatives, modifications and variations will be apparent to those skilled in the art. Accordingly, the embodiments of the invention set forth above are intended to be illustrative and not limiting. Various changes may be made without departing from the spirit and the scope of the disclosure as defined in the following claims.

What is claimed is:

1. An oxygen generating apparatus, comprising a container containing potassium super oxide, and a valve that regulates oxygen and air flow between the container and at least one of a mask or a mouthpiece, wherein the potassium super oxide comprises a mixture of potassium monoxide ($K_2O$), potassium peroxide ($K_2O_2$), and superoxide ($KO_2$), where superoxide represents about 90% to about 95% of the potassium super oxide; and wherein the apparatus is a hand-held apparatus.

2. The oxygen generating apparatus of claim 1, wherein the potassium oxide is present in an amount of about 100 g to about 200 g.

3. The oxygen generating apparatus of claim 1, wherein the potassium super oxide is present as at least one of pellets, granules, or laminated sheets.

4. The oxygen generating apparatus of claim 1, wherein the container contains at least one of graphite and carbon and at least one member selected from the group consisting of potassium super oxide granules, potassium super oxide pellets, and potassium super oxide laminated sheets.

5. The oxygen generating apparatus of claim 4, wherein the graphite is present as at least one of graphite and carbon fiber fabric.

6. The oxygen generating apparatus of claim 5, wherein the at least one of graphite and carbon fiber fabric is about 1 mm to about 6 mm thick.

7. The oxygen generating apparatus of claim 5, wherein the container contains at least one of potassium oxide granules and potassium oxide pellets, and wherein the at least one of graphite and carbon fiber fabric is layered between every 25 to 75 mm of the at least one of potassium oxide granules and potassium oxide pellets.

8. The oxygen generating apparatus of claim 5, wherein the container comprises an interior surface, a bottom, and potassium oxide laminated sheets, and wherein the at least one of graphite and carbon fiber fabric is located on the bottom and interior surface of the container.

9. The oxygen generating apparatus of claim 1, wherein the container contains at least one member selected from the group consisting of $NaO_2$, $Na_2O_2$, $Ca_2O_2$, $Ba_2O_2$, $Li_2O_2$, and anhydrous LiOH.

10. The oxygen generating apparatus of claim 1, wherein the container comprises an interior surface and an exterior surface, wherein the container is aluminum, and wherein the interior surface is coated with at least one member selected from the group consisting of polytetrafluoroethylene and an inert polymer.

11. The oxygen generating apparatus of claim 1; wherein the container comprises an interior surface and an exterior surface, and wherein the exterior surface of the container comprises a jacket comprising at least one insulant.

12. The oxygen generating apparatus of claim 11, wherein the jacket comprises silicone rubber.

13. The oxygen generating apparatus of claim 11, wherein the jacket comprises an inner surface and an outer surface, and at least one of the inner surface and the outer surface is ribbed.

14. The oxygen generating apparatus of claim 11, wherein the jacket comprises an inner surface and an outer surface, and each of the inner surface and the outer surface is ribbed.

15. The oxygen generating apparatus of claim 10, wherein the interior surface is coated with at least one member selected from the group consisting of polytetrafluoroethylene, polyethylene, and polypropylene.

16. The oxygen generating apparatus of claim 1, wherein the container contains a stainless steel tube enclosed inside of the container, and wherein the stainless steel tube contains an alloy of sodium-potassium sealed inside of the stainless steel tube.

17. The oxygen generating apparatus of claim 16, wherein the stainless steel tube has a diameter of about 6 mm and a length of about 100 mm to about 150 mm.

18. The oxygen generating apparatus of claim 1, wherein the valve includes a polymeric knob.

19. The oxygen generating apparatus of claim 1, wherein the apparatus weighs about 250 g to about 500 g.

20. An oxygen generating apparatus, comprising a container; an insulating jacket; potassium super oxide; at least one of graphite and carbon; at least one member selected from the group consisting of $NaO_2$ and $Na_2O_2$, an initiator; and a stainless steel tube containing a liquid sodium-potassium eutectic alloy.

21. An oxygen generating apparatus, comprising a container containing potassium super oxide and at least one of a catalyst, an initiator and an adjuvant; a valve that regulates oxygen and air flow between the container and at least one of a mask or a mouthpiece; wherein the apparatus is a hand-held apparatus; and wherein the amount of initiator present in the container is about 0.5% to 1.0% of the total weight of chemical compounds in the container.

22. The oxygen generating apparatus of claim 21, wherein the catalyst is selected from the group consisting of $NaO_2$, $Na_2O$, $Na_2O_2$, $Ca_2O_2$, $Ba_2O_2$, $Li_2O_2$, oxides of rubidium, and oxides of cesium.

23. The oxygen generating apparatus of claim 21, wherein the initiator is selected from the group consisting of copper oxychloride, $CuCl_2$, and CuCl.

* * * * *